United States Patent [19]
Cohen et al.

[11] Patent Number: 6,020,480
[45] Date of Patent: Feb. 1, 2000

[54] CAGED NADP AND NAD

[75] Inventors: Bruce E. Cohen, San Francisco; Daniel E. Koshland, Jr., Lafayette, both of Calif.

[73] Assignee: The Regents of the University of California, Oakland, Calif.

[21] Appl. No.: 08/974,434

[22] Filed: Nov. 20, 1997

[51] Int. Cl.⁷ .................................................. C07H 19/207
[52] U.S. Cl. .................................. 536/26.24; 536/26.23; 536/26.25
[58] Field of Search ............................ 536/26.23, 26.24, 536/26.25

[56] References Cited

U.S. PATENT DOCUMENTS

| | | | |
|---|---|---|---|
| 5,430,175 | 7/1995 | Hess et al. | 560/130 |
| 5,587,509 | 12/1996 | Hess et al. | 560/130 |
| 5,635,608 | 6/1997 | Haugland | 536/1.11 |

OTHER PUBLICATIONS

Wootton, et al., "Caged Compounds to Probe the Dynamics of Cellular Processes: Synthesis and Properties of Some Novel Photosensitive P–2–Nitrobenzyl Esters of Nucleotides", *Photochemical Probes In Biochemistry*, pp. 277–296 (1989).

McCray, et al., "A New Approach to Time–Resolved Studies of ATP–Requiring Biological Systems: Laser Flash Photolysis of Caged ATP", *Proc. Natl. Acad. Sci. USA*, vol. 77, No. 12, pp. 7237–7241 (1980).

Davis, et al., "Synthesis and Microbiological Properties of 3–Amino–1–Hydroxy–2–Indolinone and Related Compounds", *Journal of Medical Chemistry*, vol. 16, No. 9, pp. 1043–1045 (1975).

Kaplan, et al., "Rapid Photolytic Release of Adenosine 5'–Triphosphate from a Protected Analogue: Utilization by the Na:K Pump of Human Red Blood Cell Ghosts", *American Chemical Society*, vol. 17, No. 10, pp. 1929–1935 (1978).

Colowick, et al., "Preparation and Analysis of Labeled Coenzymes", *Journal of Biological Chemistry*, vol. 4, pp. 840–855 (1957).

Wieboldt, et al., "Photolabile Precursors of Glutamate: Synthesis, Photochemical Properties, and Activation of Glutamate Receptors on a Microsecond Time Scale", *Proc. Natl. Acad. Sci. USA*, vol. 91, pp. 8752–8756 (1994).

Bolduc, et al., "Mutagenesis and Laue Structures of Enzyme Intermediates: Isocitreate Dehydrogenase", *Science*, vol. 268, pp. 1312–1318 (1995).

Woenckhaus, et al., "Preparation and Properties of NAD and NADP Analogs", *Pyridine Nucleotide Coenzymes*, Chapter 13, pp. 449–568 (publishing date unknown).

Cohen, et al., "Caged NADP and NAD. Synthesis and Characterization of Functionally Distinct Caged Compounds", *Biochemistry*, vol. 36, No. 29, pp. 9035–9044 (1997).

Brubaker, et al., "Synthesis, Kinetics, and Structural Studies of a Photolabile Caged Isocitrate: A Catalytic Trigger for Isocitrate Dehydrogenase", *Biochemistry*, vol. 35, No. 9, pp. 2854–2864 (1996).

Corrie, et al., "Caged Nucleotides and Neurotransmitters", *Bioorganic Photochemistry*, vol. 2, pp. 243–305 (1993).

Duke, et al., "Time–Resolved Diffraction Studies on Glycogen Phosphorylase B", *The Royal Society*, vol. 340, pp. 245–261 (1992).

Adams, et al., "Controlling Cell Chemistry with Caged Compounds", *Annu. Rev. Physiol.*, vol. 55, pp. 755–784, (1993).

Moffat, et al., "X–Ray Laue Diffraction from Protein Crystals", *Science*, vol. 223, pp. 1423–1425 (1984).

Schlichting, et al., "Time–Resolved X–Ray Crystallographic Study of the Conformational Change in Ha–Ras p21 Protein on GTP Hydrolysis", *Nature*, vol. 345, pp. 309–315 (1990).

Trentham, et al., "A New Caged ATP with Rapid Photolysis Kinetics", *Biophys. J.*, 61, A295 [Abstract only].

Niu, et al., "Synthesis and Characterization of a Caged Receptor Ligand Suitable for Chemical Kinetic Investigations of the Glycine Receptor in the 3–$\mu$s Time Domain", *Biochemistry*, vol. 35, No. 25, pp. 8136–8142 (1996).

Mozzarelli, et al., "Protein Function in the Crystal", *Annu. Rev. Biophys. Biomol. Struct.*, vol. 25, pp. 343–365 (1996).

Reeves, et al., "NADP⁺–Specific Isocitrate Dehydrogenase of *Escherichia Coli* ", *Biochim. Biophys. Acta.*, vol. 258, pp. 27–39 (1972).

LaPorte, et al., "Compensatory Phosphorylation of Isocitrate Dehydrogenase", *The Journal for Biological Chemistry*, vol. 260, No. 19, Issue of September 5, pp. 10563–10568 (1985).

Hurley, et al., "Structure of a Bacterial Enzyme Regulated by Phosphorylation, Isocitrate Dehydrogenase", *Proc. Natl. Acad. Sci. USA*, vol. 86, pp. 8635–8639 (1989).

(List continued on next page.)

*Primary Examiner*—James O. Wilson
*Attorney, Agent, or Firm*—Beyer & Weaver, LLP

[57] ABSTRACT

Provided are caged NADP and NAD compounds. The invention includes two types of caged NAD and NADP (NAD/P) analogs, each type having a different caging group binding at a different site on the molecule: Phosphate-caged DMNPE-NAD/P and nicotinamide-caged CNB-NAD/P. Both types of caged molecules are designed to be inactive in their caged configurations and activated upon photolysis of the caging group. In some applications, the different types of caged compounds may exhibit biochemically distinct activities. For example, "catalytically caged" NAD/P compounds according to the present invention may bind to an enzyme but not allow turnover prior to photolytic activation. This type of compound has the advantage, when used as a photolytic trigger for time-resolved studies, that it is bound to the enzyme active site prior to photolysis so that no additional diffusion or binding events are necessary to form the Michaelis complex. The present invention also provides NAD/P compounds which may be "affinity caged," having no interaction with the enzyme prior to photolysis. In addition, the invention provides methods of synthesizing caged NAD and NADP and methods of using these compounds in biomedical research applications.

23 Claims, 8 Drawing Sheets

OTHER PUBLICATIONS

Stoddard, et al., "Structure of Isocitrate Dehydrogenase with Isocitrate, Nicotinamide Adenine Dinucleotide Phosphate, and Calcium at 2.5–Å Resolution: A Pseudo–Michaelis Ternary Complex", *Biochemistry*, vol. 32, pp. 9310–9316 (1993).

Hurley, et al., "Regulation of an Enzyme by Phosphorylation at the Active Site", *Science*, vol. 249, pp. 1012–1016 (1990).

Hurley, et al., "Regulation of Isocitrate Dehydrogenase by Phosphorylation Involves No Long–Range Conformational Change in the Free Enzyme", *The Journal of Biological Chemistry*, vol. 265, No. 7, pp. 3599–3602 (1990).

Hurley, et al., "Catalytic Mechanism of $NADP^+$–Dependent Isocitrate Dehydrogenase: Implications from the Structures of Magnesium–Isocitrate and $NADP^+$–Complexes", *Biochemistry*, vol. 30, pp. 8671–8678 (1991).

Stoddard, et al., "Structure of Isocitrate Dehydrogenase with α–Ketoglutarate at 2.7–Å Resolution: Conformational Changes Induced by Decarboxylation of Isocitrate", *Biochemistry*, vol. 32, pp. 9317–9322 (1993).

Brünger, et al., "Crystallographic R Factor Refinement by Molecular Dynamics", *Science*, vol. 235, pp. 458–460 (1986).

F.C. Bernstein, et al., "The Protein Data Bank: A Computer–Based Archival File for Macromolecular Structures", *Journal of Molecular Biology*, vol. 112, pp. 535–542 (1977).

Zatman, et al., "Inhibition of Spleen Diphosphopyridine Nucleotidase by Nicotinamide, An Exchange Reaction", *J. Biochem.*, 200, pp. 197–212 (1952).

Aarhus, et al., "Caged Cyclic ADP–Ribose", *The Journal of Biological Chemistry*, vol. 270, No. 13, pp. 7745–7749 (1995).

Lee, et al., "Caged Nicotinic Acid Adenine Dinucleotide Phosphate", *The Journal of Biological Chemistry*, vol. 272, No. 7, pp. 4172–4178 (1997).

Nerbonne, et al., "New Photoactivatable Cyclic Neucleotides Produce Intracellular Jumps in Cyclic AMP and Cyclic GMP Concentrations", *Nature*, vol. 310, pp. 74–76 (1984).

Hurley, et al., "Actinometry in Monochromatic Flash Photolysis: the Extinction CoEfficient of Triplet Benzophenone and Quantum Yield of Triplet Zinc Tetraphenyl Porphyrin", *Photochemistry and Photobiology*, vol. 38, No. 1, pp. 9–14 (1983).

Walker, et al., "Photolabile Protecting Groups for an Acetylcholine Receptor Ligand. Synthesis and Photochemitry of a New Class of o–Nitrobenzyl Derivatives and Their Effects on Receptor Function", *Biochemistry*, vol. 25, pp. 1799–1805 (1986).

Milburn, et al., "Synthesis, Photochemistry, and Biological Activity of a Caged Photolabile Acetycholine Receptor Ligand", *Biochemistry*, vol. 28, pp. 49–55 (1989).

Bernofsky, et al., "An Improved Cycling Assay for Nicotinamide Adenine Dinucleotide", *Analytical Biochemistry*, vol. 53, pp. 452–458 (1973).

Nisselbaum, et al., "A Simple Ultramicro Method for Determination of Pyridine Nucleotides in Tissues", *Analytical Biochemistry*, vol. 27, pp. 212–217 (1969).

Dietrich, et al., "Pyridine Nucleotide Metabolism: Mechanism of Action of the Niacin Antagonist, 6–Aminonicotinamide", *Pyridine Nucleotide Metabolism*, vol. 233, No. 4, pp. 964–968 (1958).

Walker, et al., "Rapid Release of an α–Adrenergic Receptor Ligand from Photolabile Analogues", *Biochemistry*, vol. 32, No. 5, pp. 1338–1345 (1993).

McCray, et al., "Properties and Uses of Photoreactive Caged Compounds", *Annu. Rev. Biophys. Chem.*, vol. 18, pp. 239–270 (1989).

Goldman, et al., "The Role of Thiols in Caged–ATP Studies and Their Use in Measurement of the Photolysis Kinetics of o–Nitrobenzyl Compounds", *Biophysical Journal*, vol. 37, p. 125a (1982) [Abstract only].

Walker, et al., "Photolabile 1–(2–Nitrophenyl)Ethyl Phosphate Esters of Adenine Nucleotide Analogues. Synthesis and Mechanism of Photolysis" *Journal of American Chemical Society*, vol. 110, No. 21, pp. 7170–7177 (1988).

Wilcox, et al., "Synthesis of Photolabile 'Precursors' of Amino Acid Neurotransmitters", *J. Org. Chem.*, vol. 55, No. 5, pp. 1585–1589 (1990).

Ramesh, et al., "Photolabile Precursors of Biological Amides: Synthesis and Characterization of Caged O–Nitrobenzyl Derivatives of Glutamine, Asparagine, Glycinamide, and γ–Aminobutramide", *J. Org. Chem.*, vol. 58, No. 17, pp. 4599–4605 (1993).

Bruce M. Anderson, "Analogs of Pyridine Nucleotide Coenzymes", *The Pyridine Nucleotide Coenzymes*, pp. 92–133 (1982).

CAGED NADP AND NAD

This invention was made with Government support under Grant (Contract) No. 04200 awarded by the National Science Foundation. The Government has certain rights to this invention.

BACKGROUND OF THE INVENTION

This invention relates generally to biochemical compounds, and in particular to caged compounds. More specifically, the invention relates to caged NADP and NAD.

The pyridine nucleotides nicotinamide adenine dinucleotide (NAD) and nicotinamide adenine dinucleotide phosphate (NADP) are the most abundant coenzymes in eukaryotic cells and have long been studied as oxidative cofactors. These pyridine nucleotides (referred to herein as "the pyridine nucleotide coenzymes") serve as cofactors for all known dehydrogenases and many reductases and hydroxylases, making them the major carriers of protons ($H^+$) and electrons ($e^-$) in a number of major metabolic systems, including the glycolysis pathway, the tricarboxylic acid cycle, fatty acid synthesis, and sterol synthesis. NAD and NADP generally have distinct physiological roles. Oxidation of NADH to NAD releases an electron pair which ultimately results in the formation of ATP, making NAD the major cellular energy source for oxidative phosphorylation. NADP, on the other hand, plays a central role in moving electrons along reductive cellular metabolic pathways.

The pyridine nucleotide coenzymes also have an assortment of non-redox functions. For example, NAD is the substrate for poly (ADP-ribose) synthetase, which adds poly ADP-ribose to chromatin and other nuclear proteins in eukaryotic cell nuclei. In this function NAD plays an important role in DNA repair, cell differentiation and DNA synthesis. NAD also serves as the substrate the mono ADP-ribosylation of host proteins by pathogenic bacteria and for the poly ADP-ribosylation of chromatin. Both NAD and NADP are involved in the phagosomal production of oxygen radicals in neutrophils, and are precursors to compounds involved in a complex process of regulating calcium ($Ca^{+2}$) mobilization.

The importance of the pyridine nucleotide coenzymes is reflected in the extraordinary number of analogs which have been synthesized to study their various functions. To date, approximately 200 NADP and NAD analogs have been constructed, including fluorescent derivatives, structural analogs, affinity labels, and spin-labeled analogs. In addition, dozens of derivatives with substituted or altered nicotinamide have been constructed and used to investigate the redox potential of hydride transfer and to study coenzyme binding sites. However, no successful "caged" NAD and NADP compounds are known.

"Caged" compounds are biologically inactive molecules designed to fragment into biologically active molecules upon photolysis. The strategy of adding photolabile groups to biomolecules has been an invaluable resource since Hoffmann and coworkers introduced caged ATP in 1978 (Kaplan, J. H., Forbush, B. d., and Hoffman, J. F. (1978) *Biochemistry* 17, 1929–1935). A review of known caged compounds is provided by Corrie, J. E. T. and Trentham, D. R. (1993) in *Bioorganic Photochemistry* Volume 2: *Biological Applications of Photochemical Switches* (Morrison, H., Ed.) pp 243–305, John Wiley & Sons, Inc., New York, which is incorporated herein by reference for all purposes. As inert compounds, caged molecules can be introduced into biological systems over relatively long periods and then be activated rapidly by light, providing a means of exerting temporal and spatial control over the introduction of physiologically active compounds into complex systems. This approach has proven invaluable in systems where traditional methods of rapid mixing are not possible, such as with membrane preparations, living cells, tissue slices, and protein crystals.

Caged compounds are typically constructed by covalently modifying a biologically active molecule with a photolabile protecting, or "caging", group. Given the function of caged compounds, the key characteristics of an effective caging group are its ability to render the substrate inert in the particular system being studied, and to then release it rapidly and efficiently following photolysis. It is also advantageous if the caging group has an absorbance spectrum different enough from the compound being caged so that photolysis interference is avoided, and if it is unreactive with surrounding proteins when released.

One important application of caged compounds is in determining the structures of short-lived enzymatic intermediates using time-resolved Laue crystallography. This technique is described, for example, in Moffat, K., Szebenyi, D., and Bilderback, D. (1984) *Science* 223, 1423–1425, which is incorporated by reference herein for all purposes. Irradiation of protein crystals soaked with caged compounds can rapidly initiate synchronous turnover within the crystal, allowing catalytic intermediates to be visualized crystallographically. For example, caged GTP has been used to characterize the GTPase activity of Ha-ras p21 protein, as described in Schlichting, I., Almo, S. C., Rapp, G., Wilson, K., Petratos, K., Lentfer, A., Wittinghofer, A., Kabsch, W., Pai, E. F., Petsko, G. A., and Goody, R. S. (1990) *Nature* 345, 309–315.

Accordingly, caged NADP and NAD compounds would be desirable in many areas of biomedical research. Moreover, the ability to design caged NAD/P compounds with biochemically distinct activities could be advantageous for some applications of these compounds.

SUMMARY OF THE INVENTION

To achieve the foregoing, the present invention provides caged NADP and NAD compounds. In preferred embodiments, the invention includes two types of caged NAD and NADP (NAD/P) analogs, each type having a different caging group binding at a different site on the molecule: Phosphate-caged DMNPE-NAD/P and nicotinamide-caged CNB-NAD/P. Both types of caged molecules are designed to be inactive in their caged configurations and activated upon photolysis of the caging group.

In some applications, the different types of caged compounds may exhibit biochemically distinct activities. For example, "catalytically caged" NAD/P compounds according to the present invention may bind to an enzyme but not allow turnover prior to photolytic activation. This type of compound has the advantage when used as a photolytic trigger for time-resolved studies that it is bound to the enzyme active site prior to photolysis, so that no additional diffusion or binding events are necessary to form the Michaelis complex. The present invention also provides NAD/P compounds which may be "affinity caged," having no interaction with the enzyme prior to photolysis.

In addition, the invention provides methods of synthesizing caged NAD and NADP and methods of using these compounds in biomedical research applications.

In one preferred embodiment, the present invention provides a biologically inactive chemical compound which fragments into a biologically active compound upon photolysis. The compound includes a pyridine nucleotide coenzyme covalently bonded to a 2-nitrobenzyl family caging group.

These and other features and advantages of the present invention will be presented in more detail in the following specification of the invention and the accompanying figures which illustrate by way of example the principles of the invention.

BRIEF DESCRIPTION OF THE DRAWINGS

FIGS. 10A–F show electron density maps of crystallographic studies of caged CNB-NADP and DMNPE-NADP compounds according to preferred embodiments of the present invention binding to the active site of IDH.

DETAILED DESCRIPTION OF THE PREFERRED EMBODIMENTS

The caged NADP and NAD compounds of the present invention will now be described with reference to several preferred embodiments. Important properties and characteristics of the preferred embodiments are illustrated in the structures in the text and in the accompanying drawings. While the invention will be described in conjunction with these preferred embodiments, it should be understood that the invention it is not intended to be limited to these preferred embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The following abbreviations are used in this detailed description: NADP, nicotinamide adenine dinucleotide phosphate; NAD, nicotinamide adenine dinucleotide; IDH, isocitrate dehydrogenase (*Escherichia coli*); ADP, adenine dinucleotide phosphate; ATP, adenine trinucleotide phosphate; FAB+, fast atom bombardment; NHS, N-hydroxysuccinimide; DMF, dimethylformamide; EDC, 1-(3-dimethylaminopropyl)-3-ethylcarbodiimide hydrochloride; CNB, α-carboxy-2-nitrobenzyl; MWCO, molecular weight cut-off; HRMS, high resolution mass spectrum; DMNPE, 1-(4,5-dimethoxy-2-nitrophenyl)ethyl; DMNPDE, 1-(4,5-dimethoxy-2-nitrophenyl)diazoethane; DMNB, 1-(4,5-dimethoxy-2-nitrobenzyl); G6PD, glucose-6-phosphate dehydrogenase; DTT, dithiothreitol.

As noted above, the present invention provides caged NADP and NAD compounds. Preferred embodiments of the invention include two types of caged NAD and NADP (NAD/P) analogs, both types having a caging group from the 2-nitrobenzyl family, and each type having the different 2-nitrobenzyl family caging group binding at a different site on the molecule: Phosphate-caged DMNPE-NAD/P and nicotinamide-caged CNB-NAD/P. Both types of caged molecules are designed to be inactive in their caged configurations and activated upon photolysis of the caging group. The invention also provides methods of synthesizing caged NAD and NADP and methods of using these compounds in a variety of biomedical research applications.

Phosphate-Caged DMNPE-NAD/P

1

Structure 1 illustrates a caged NADP compound according a preferred embodiment of the present invention. The structure is a NADP derivative with its 2'- phosphate group esterified with a 1-(4,5-dimethoxy-2-nitrophenyl)ethyl (DMNPE) group.

The corresponding phosphate-caged NAD has two structural isomers illustrated as structures 2a and 2b, below. The DMNPE group bonds to either of the phosphates of the diphosphate backbone.

These phosphate caged compounds may be synthesized by alkylation of NADP and NAD with the highly labile and photosensitive diazo compound 1-(4,5-dimethoxy-2-nitrophenyl)diazoethane (DMNPDE), which shows strong reactivity toward the weakly nucleophilic oxygens of nucleotide phosphates. DMNPDE may be prepared by oxidation of the corresponding hydrazone (4,5-dimethoxy-2-nitroacetophenylhydrazone) with $MnO_2$ in $CHCl_3$, such as is described in Wilcox, M., Viola, R. W., Johnson, K. W., Billington, A. P., Carpenter, B. K., McCray, J. A., Guzikowski, A. P., and Hess, G. P. (1990) *J. Org. Chem.* 55, 1585–1589, which is incorporated herein by reference for all purposes.

Figure 1:
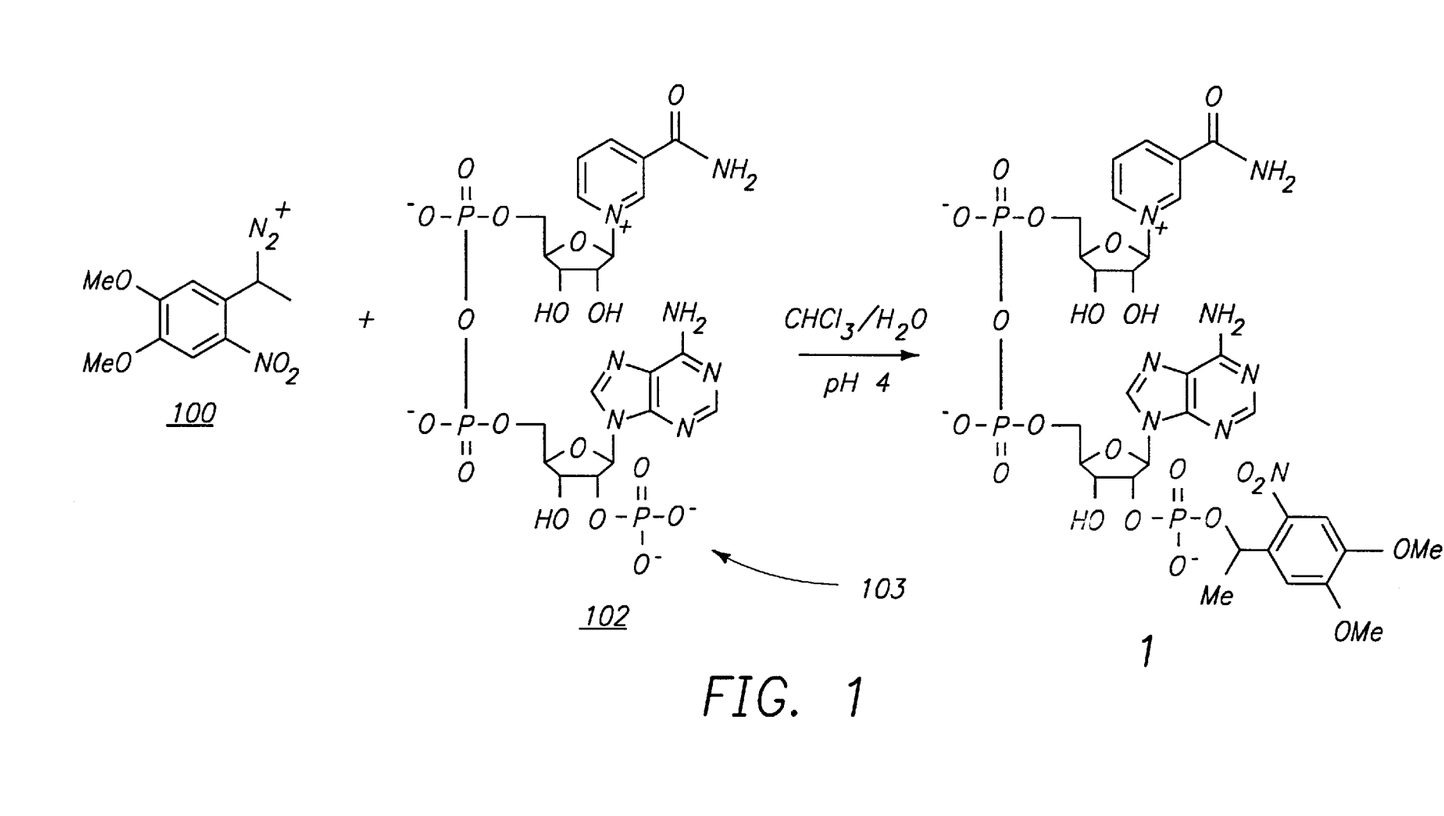
FIG. 1 schematically depicts a synthesis of phosphate-caged DMNPE-NADP according to a preferred embodiment of the present invention.

A preferred synthesis of phosphate-caged DMNPE-NADP is illustrated in FIG. 1. DMNPDE 100 dissolved in $CHCl_3$ formed as noted above is filtered directly into a stirring aqueous solution of NADP 102 at a pH of about 4. At pH 4, the solution is sufficiently acidic to allow the 2'-phosphate group 103 on NADP 102 to react with the DMNPDE 100 in a biphasic reaction, displacing $N_2$ to produce DMNPE-NADP 1.

Figure 2:
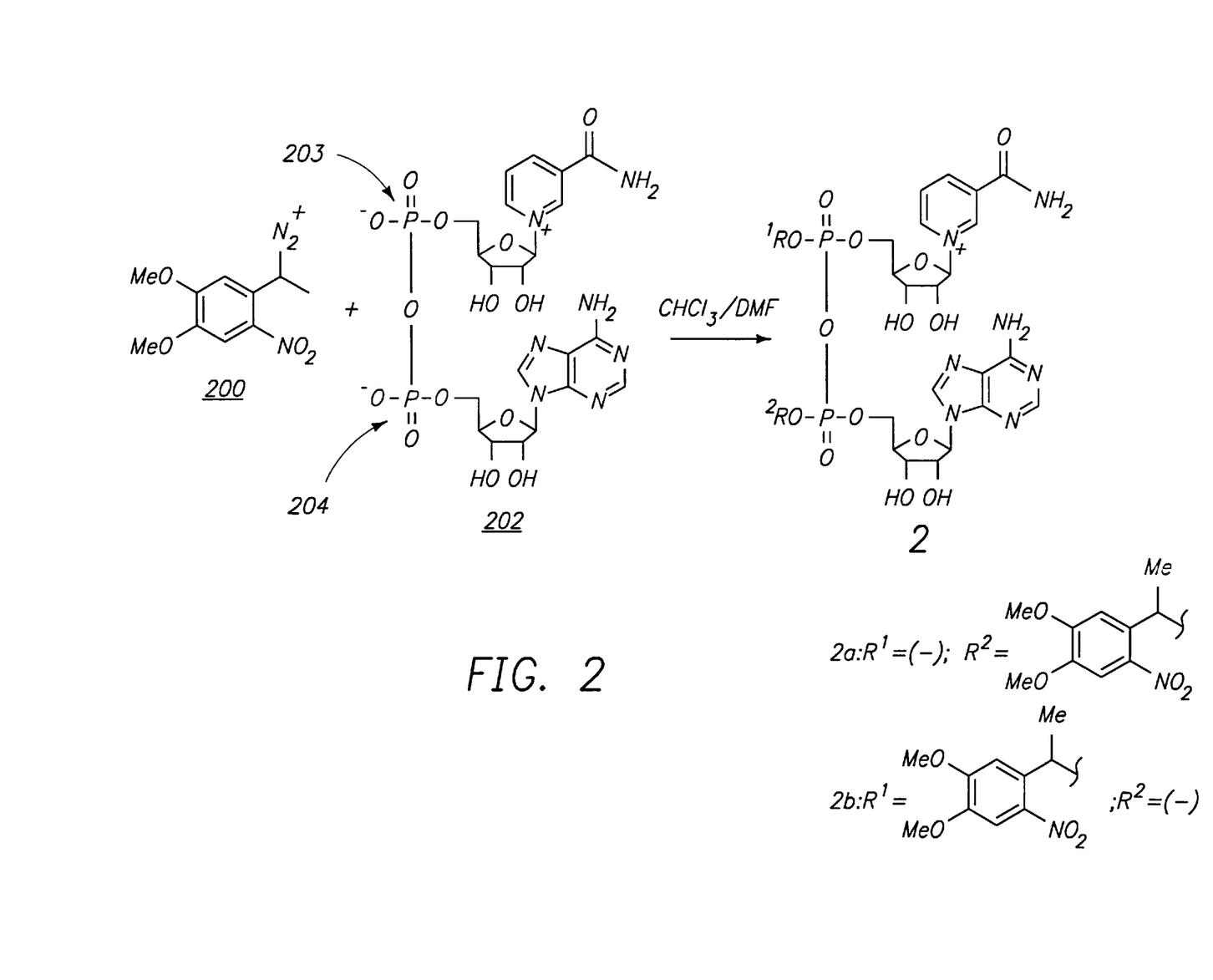
FIG. 2 schematically depicts a synthesis of phosphate-caged DMNPE-NAD according to a preferred embodiment of the present invention.

As shown in FIG. 2, DMNPDE 200 reacts with a phosphate group on NAD 202 to produce DMNPE-NAD 2 according to an analogous reaction. However, since NAD has no 2'-phosphate group to react with DMNPDE, and the oxygens of the acidic backbone diphosphate groups 203, 204 are unreactive toward DMNPDE under the biphasic reaction conditions used to prepare DMNPE-NADP, different reaction conditions are required. Alkylation of NAD, such as by replacement of the standard $Na^+$ salt of NAD with tetrabutylammonium, renders NAD soluble in organic media, where the reactivity towards DMNPDE of the oxygens on either of its backbone phosphate groups is increased. As noted above, the product of this reaction is an isomeric mixture of structures 2a and 2b. The aqueous solubility of the caged NAD compound may be restored during purification when any remaining tetrabutylammonium is replaced by ammonium.

Nicotinamide-Caged CNB-NAD/P 3-(R = $PO_3^{-2}$)
4-(R = H)

Figure 3:
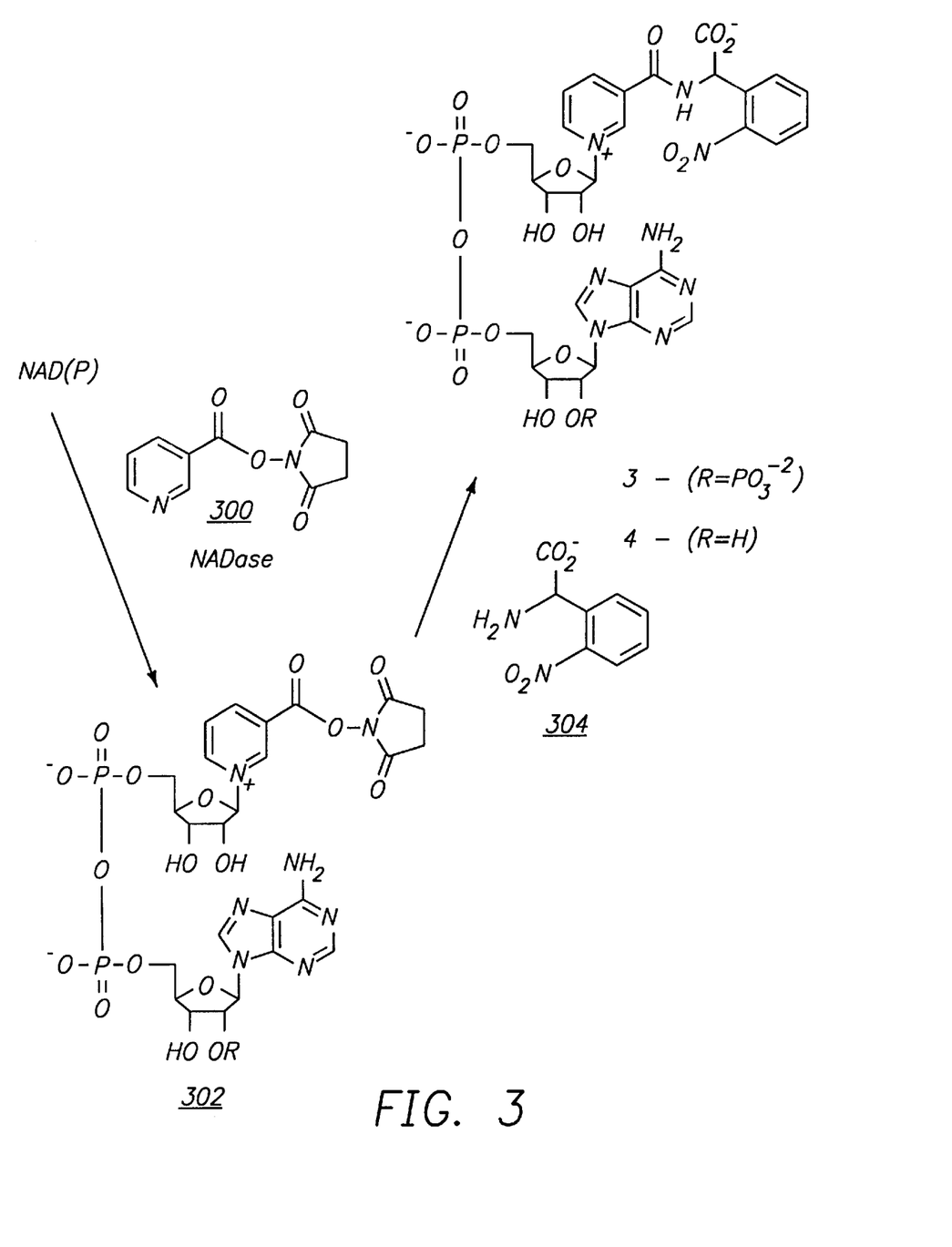
FIG. 3 schematically depicts a synthesis of nicotinamide-caged CNB-NAD/P according to a preferred embodiment of the present invention.

The nicotinamide-caged CNB-NADP 3 and CNB-NAD 4, illustrated above, may be synthesized by an enzymatic reaction using NADase, a glycohydrolase that is able to catalyze an unusual exchange reaction of synthetic nicotinamide groups onto either NADP or NAD. Previous attempts to cage NAD/P by a direct route using NADase have proved unsuccessful. As illustrated in FIG. 3, the reaction of the present invention proceeds by a two-step process starting with the NADase-catalyzed exchange of activated ester NHS nicotinate 300 onto NADP or NAD, yielding NHS-NAD/P 302.

It is believed that this NHS-NAD/P intermediate 302 has the potential to be elaborated into a variety of other compounds, effectively overcoming steric limitations previously encountered with this NADase exchange reaction and greatly expanding its scope. For example, NHS-NAD/P 302 could potentially be attached to amino linkers on beads for use in affinity chromatography.

In the second step of the present synthesis, crude NHS-NAD/P 302 may be treated with 2-nitrophenylglycine 304 following the first step, to produce caged CNB-NAD/P ¾.

Photolysis

Figure 4:
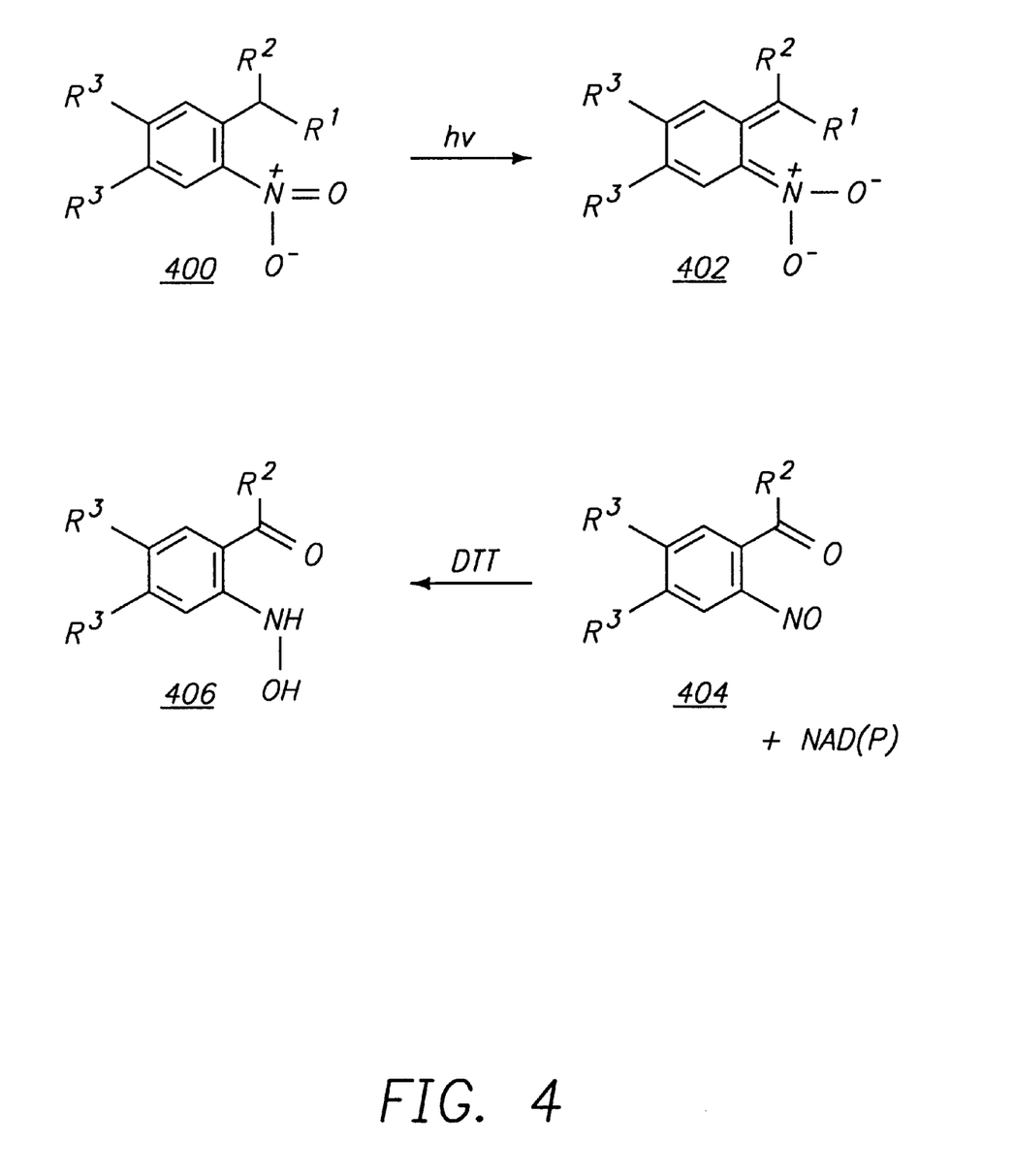
FIG. 4 schematically depicts the general mechanism of photocleavage of 2-nitrobenzyl-caged compounds, such as occurs upon photolysis of DMNPE- and CNB-caged NAD/P compounds according to a preferred embodiment of the present invention.

Photolysis of DMNPE- and CNB-caged NAD/P is believed to occur by the general mechanism of photocleavage of 2-nitrobenzyl caged compounds, illustrated in FIG. 4. Following excitation by irradiation with light of an appropriate wavelength, a caged compound 400 fractures into nitrosoketone 404 and NAD/P via an aci-nitro anion 402. In the presence of DTT, compound 404 is reduced to compound 406, which is useful in the photospectroscopic detection of NAD/P upon photolysis of the caged compounds. $R^1$ is NADP or NAD. For compounds 1 and 2, $R^2$=Me and $R^3$=OMe. For compounds 3 and 4, $R^2$=$CO_2^-$ and $R^3$=H.

The photolyzable DMNPE group has a maximum absorbance at a wavelength ($\lambda$) of about 350 nm. This absorbance characteristic makes the DMNPE group particularly suitable as a caging group for NADP and NAD. First of all, several common irradiating systems known in the art produce light with a wavelength at or near this maximum absorbance value. These radiation sources include a frequency-doubled ruby laser ($\lambda$=347 nm), a frequency-tripled neodymium: YAG laser ($\lambda$=355 nm), and a XeF excimer laser ($\lambda$=351 nm). Other suitable photolytic light sources include lamps, such as flash lamps, having either a focused or a broad wavelength spectrum. A second advantage of the DMNPE caging group is that this maximum absorbance is sufficiently removed from the main absorbance wavelengths of other groups on the caged molecule (such as nicotinamide and adenine which maximally absorb at about 266 nm) that photolysis occurs with minimum interference from other absorbing groups. Generally, irradiation in the range of about 260 to 400 nm, more preferably about 300 to 370 nm, and most preferably about 350 nm may be used for photolysis according to this embodiment of the present invention.

Figure 5:
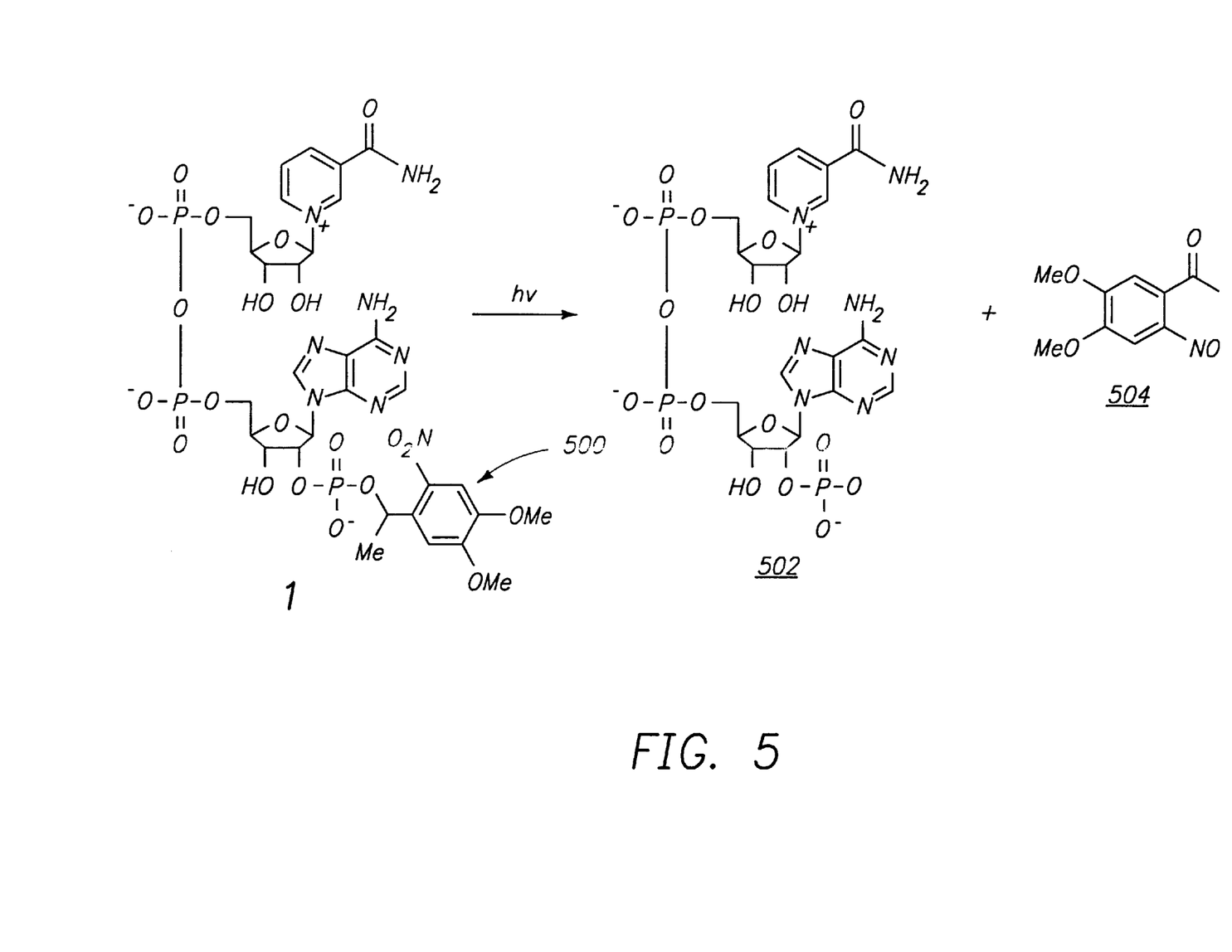
FIG. 5 schematically depicts the photolysis of DMNPE-caged NADP according to a preferred embodiment of the present invention.

Photolysis of DMNPE-caged NADP is illustrated in FIG. 5. As noted above, the photolysis is believed to occur according to a general mechanism of cleavage of 2-nitrobenzyl caged compounds, via an aci-nitro anion to a nitrosoketone. The DMNPE group 500 absorbs light and fragments, releasing NADP 502 and nitrosoketone by-product 504. DMNPE-caged NAD photolyzes by the same mechanism.

The photolyzable CNB group has a maximum absorbance at a wavelength of about 266 nm. While this maximum absorbance wavelength does not distinguish the CNB group from the nicotinamide and adenine groups of the caged molecule, the CNB group's absorbance spectrum is higher than that of the other absorbing groups in the molecule above 300 nm. This absorbence characteristic may be exploited to reduce interference from other absorbing groups in the molecule during photolysis of CNB-caged NAD/P by selecting a radiation source having a wavelength above 300 nm. Such radiation sources include a those preferred sources described above for photolysis of DMNPE-caged NAD/P. In addition, a dye laser ($\lambda$=320 nm) may be particularly useful for photolysis of CNB-caged NAD/P.

Applications

The caged NAD/P compounds of the present invention may find use in a variety of basic biomedical research and other applications. As inert compounds, caged molecules may be introduced into biological systems over relatively long time periods and then be activated rapidly by light. This provides the ability to exert a high degree of control over the introduction of physiologically active compounds into complex systems. This approach is particularly valuable where traditional methods of rapid mixing are not effective or not possible, such is with membrane preparations, living cells, tissue slices, or protein crystals. The present invention also provides NAD/P compounds which are activated by photolytic fragmentation in the millisecond time range, thereby offering superior time resolution to other mixing methods. Among the biomedical research applications of the caged compounds of the present invention are the study of enzyme mechanics, cell differentiation, phagocytosis, $Ca^{2+}$ mobilization, cell metabolism, and bacterial pathogenesis.

In one preferred embodiment, caged NAD/P compounds according to the present invention may be used to study enzyme mechanics and kinetics. A NAD/P coenzyme required for enzyme activity may be provided to the environment of an enzyme in a caged form and photolytically activated at a desired time. Laue crystallography, for example, may be used to collect data. For example, in this way, Laue crystallography may be used in the study of isocitrate dehydrogenase (IDH), an NADP-dependent enzyme of the tricarboxylic acid cycle which converts isocitrate to α-ketoglutarate. This example also illustrates the utility of the distinct biochemical activity that may be conferred upon caged NAD/P compounds according to the present invention by different caging groups. A nicotinamide caged CNB-NADP acts as a catalytically caged compound binding to IDH, but not allowing turnover prior to photolytic activation. A phosphate caged DMNPE-NADP, on the other hand, behaves as an affinity caged compound having no interaction with IDH prior to photolysis.

EXAMPLES

The following examples provide details concerning the synthesis and characteristics of the compounds in accordance with the present invention. It should be understood the following is representative only, and that the invention is not limited by the detail set forth in these examples.

Caged compounds according to the preferred embodiments of the present invention described above have been prepared and analyzed as follows. Unless otherwise noted, all materials were obtained from commercial suppliers and used without further purification. Organic reaction solvents were dried over 4 Å sieves immediately prior to use. Reverse phase HPLC was performed with a Vydac $C_{18}$ semi-preparative column with a Waters model 441 absorbance detector. $^1H$ NMR spectra were determined at 400 or 500 MHz on Bruker superconducting FT spectrometers, and $^{31}P$ NMR spectra were determined at 162 MHz. The internal reference for $^1H$ spectra was tetramethylsilane; the external reference for $^{31}P$ NMR spectra was 85% $H_3PO_4$. Chemical shifts are reported in δ values, positive values indicating shifts downfield from standard. $^1H$ NMR spectra are tabulated in order: multiplicity (s, singlet; d, doublet; t, triplet; m, multiplet; app, apparent), coupling constant(s) in Hertz, number of protons. FAB+mass spectra were recorded at the UC Berkeley Mass Spectral Laboratory on an AE1 M512 mass spectrometer. Mass spectral data are reported as m/z for the molecular ion. Elemental analyses were performed by the Microanalytical Laboratory, operated by the College of Chemistry, University of California, Berkeley.

Example 1

Synthesis of P$^{2'}$-[1-(4,5-Dimethoxy-2-nitrophenyl) ethyl]nicotinamide adenine dinucleotide phosphate (DMNPE-NADP, 1)

NADP (575 mg, 0.75 mmol) was dissolved in 3 mL of H$_2$O, and the solution was adjusted to pH 4 with 1.0 M NaOH. In a separate flask, 300 mg (1.25 mmol) of 4,5-dimethoxy-2-nitroacetophenylhydrazone (16) was stirred in 3 mL of CHCl$_3$ in the dark, and 688 mg (8.00 mmol) of MnO$_2$ was added. The suspension was stirred for 5 min and then the resulting 1-(4,5-dimethoxy-2-nitrophenyl) diazoethane (DMNPDE) was filtered through Celite into the stirring NADP solution. The two-phase solution was stirred well in the dark for 2 h. The solution was readjusted to pH 4 with 0.5 M HCl and then DMNPDE from 100 mg (0.42 mmol) more hydrazone was filtered through Celite into the solution. The two-phase solution was stirred well in the dark overnight, the organic layer removed, and the aqueous layer washed with CHCl$_3$ (2×3 mL). The aqueous layer was then added to a DEAE anion-exchange column (acetate form) and eluted with a linear gradient from 0 to 1 M NH$_4$OAc, pH 5.8. Fractions were assayed for absorbance at both 266 and 365 nm. Only one series of fractions showed strong absorbances at both wavelengths; they were pooled and concentrated. Analysis by reverse phase HPLC (3 mL/min; 0 to 10 min, 20 mM NaOAc, pH 5.6; 10 to 18 min, a linear gradient to 15% MeOH; 18 min onward, 15% MeOH) showed a single compound eluting at 28.1 min. To remove excess NH$_4$OAc, the residue was taken up repeatedly in 95% ethanol and concentrated. The residue was then dissolved in 10 mL of water and added to 200 mL of a 1:1 acetone/EtOH mixture at −20° C., causing 566 mg (59%) of product to precipitate as a waxy yellow solid: $^1$H NMR (D$_2$O, 400 MHz) δ9.04 (s, 1H), 8.78 (s, 1H), 8.58 (d, J=7.5, 1H), 8.08 (d, J=12.8, 1H), 7.91 (t, J=7.1, 1H), 7.69 (d, J=12.3, 1H), 7.09 (s, 1H), 6.67 (d, J=10.5, 1H), 5.77 (d, J=4.9, 1H), 5.58 (m, 2H), 4.99 (m, 1H), 4.38 (m, 1H), 4.25 (m, 1H), 4.20 (m, 2H), 4.12 (m, 1H), 4.02–3.95 (m, 4H), 3.64 (m, 6H), 1.19 (d, J=6.1, 3H); $^{31}$P NMR (D$_2$O with 50 mM NaOAc, pH 5.8, 162 MHz) δ−1.51, −11.10 (A-B, J=20.4); $\epsilon_{355}$=3900 M$^{-1}$ cm$^{-1}$; HRMS (FAB, MH$^+$) calc for C$_{31}$H$_{40}$N$_8$O$_{21}$P$_3$, 953.1521 found, 953.1516.

Example 2

Synthesis of P-[1-(4,5-Dimethoxy-2-nitrophenyl) ethyl] nicotinamide adenine dinucleotide (DMNPF-NAD, 2a,b)

NAD (500 mg, 0.75 mmol) was converted to its tetrabutylammonium salt by passing it over a (nBu)$_4$N$^+$ AG-1 column, eluting with water. UV-absorbant fractions were pooled and concentrated; the resulting oil was taken up 3 times in dry DMF and concentrated to a white solid. This solid was stirred in 7.5 mL of dry DMF under N$_2$. In a separate flask, 359 mg (1.50 mmol) of 4,5-dimethoxy-2-nitroacetophenylhydrazone was stirred in 3 mL of CHCl$_3$ in the dark, and 500 mg (5.81 mmol) of MnO$_2$ was added. The suspension was stirred for 5 min and then the resulting DMNPDE was filtered through Celite into the stirring NAD suspension. The CHCl$_3$ was then carefully removed from the mixture with a rotary evaporator. The remaining DMF solution wars stirred vigorously in the dark for 18 h, concentrated, and the residue partitioned between 10 mL of CHCl$_3$ and 20 mL of 50 mM NaOAc, pH 5.6. The aqueous layer was washed with 2×10 mL of CHCl$_3$ and concentrated to dryness. The yellow residue was resuspended and chromatographed on a DEAE anion-exchange column (acetate form), eluting with a linear gradient from 0 to 400 mM NH$_4$OAc, pH 5.8. Fractions were assayed for absorbance at both 266 and 365 nm. The earlier of two series of fractions showing strong absorbances at both wavelengths was pooled and concentrated. Analysis by reverse phase HPLC (with elution conditions for 1) showed a single broad peak centered at 29.4 min. To remove NH$_4$OAc, the residue was taken up repeatedly in 95% ethanol and concentrated, and then lyophilized from water, resulting in 370 mg (55%) of yellow oil as a mixture of structural isomers as determined by $^{31}$P NMR: $^1$H NMR (D$_2$O, 400 MHz) δ9.10 (s, 1H), 8.92 (d, J=5.5, 1H), 8.59 (d, J=7.9, 1H), 8.12 (s, 1H), 7.97 (d, J=6.9, 1H), 7.75 (s, 1H), 7.10 (d, J=11.2, 1H), 6.92 (d, J=10.5, 1H), 5.86 (d, J=5.0, 1H), 5.71 (d, J=5.3, 1H), 4.47–3.95 (m, 10H), 3.64 (m, 6H), 1.21 (d, J=6.0, 3H); $^{31}$P NMR (D$_2$O with 50 mM NaOAc, pH 5.8, 162 MHz) δ−0.44 (m), −10.96 (m); $\epsilon_{355}$=4000 M$^{-1}$ cm$^{-1}$; mass spectrum (FAB+): 907 (M.NH$_4$)$^+$.

Example 3

Synthesis of N-(α-Carboxy-2-nitrobenzyl)-nicotinamide adenine dinucleotide phosphate (CNB-NADP, 3)

A two-step synthesis from NADP involving the NADase-catalyzed exchange of activated ester NHS nicotinate onto NADP, yielding NHS-NADP, followed by the treatment of crude NHS-NADP with 2-nitrophenylglycine.

Step 1 (a) Synthesis of NHS nicotiniate. Nicotinic acid (3.00 g, 24.4 mmol) and NHS alcohol (3.10 g, 27.0 mmol) were dissolved in 25 mL of dry DMF. Fresh EDC (5.06 g, 26.3 mmol) was added, and the solution stirred for 10 h under N$_2$. The solution was concentrated and the residue partitioned between CH$_2$Cl$_2$ and brine. The organic layer was dried, filtered, and concentrated to an off-white solid, which was purified by chromatography on silica gel eluting with ether, affording 5.16 g (96%) of white solid: $^1$H (CDCl$_3$, 500 MHz) δ9.30 (d, J=1.7, 1H), 8.87 (dd, J=4.9, 1.7, 1H), 8.37 (app dt, J=8.0,1.8, 1H), 7.46 (ddd, J=7.9, 4.8, 1.7, 1H), 2.90 (s, 4H). Anal. Calc for C$_{10}$H$_8$N$_2$O$_4$: C, 54.55; H, 3.66; N, 12.72. Found: C, 54.24; H, 3.73; N, 12.62.

Step 1 (b) Synthesis of (N-Hydroxysuccinimide nicotinate) adenine dinucleotide phosphate (NHS-NADP). NHS nicotinate (1.20 g, 5.46 mmol) was dissolved in 8 mL of acetone and 2 mL of water; this was added to 600 mg (0.78 mmol) of NADP dissolved in 115 mL of 400 mM phosphate buffer, pH 7.2. NADase (1.2 g, 11 U) was added and the mixture shaken at 37° C. After 30 min the pH had fallen to 6.9 and was carefully readjusted to 7.1. The reaction was monitored for the loss of NADP by removal of a 10-μL aliquot every half hour for analysis by the glucose-6-phosphate dehydrogenase (G6PD) assay, as described below. After 4 h the mixture was cooled to 4° C. and spun at 4000×g for 5 min. The supernatant was concentrated to 40 mL with a rotary evaporator and spun at 12000×g for 10 min. The supernatant was then added to 180 mL of cold acetone and chilled at −20° C. for 1 h. The precipitate was pelleted at 12000×g, washed once with cold acetone, and dried under vacuum. This solid was used in the next step without further purification.

Step 2 Synthesis of (CNB-NADP, 3). A solution of 300 mg (1.19 mmol) of 2-nitrophenylglycine in 5 mL of 100 mM phosphate buffer, pH 7.2, was added to half of the crude NHS ester precipitate from the previous reaction (final solution pH=6.5). The mixture was stirred for 2 h and centrifuged at 4000×g for 5 min. The supernatant was then passed through an Amicon YM10 ultrafiltration membrane which had been carefully rinsed to remove all $NaN_3$. The filtrate was dialyzed extensively against water (Spectrum dialysis tubing, MWCO 500) and then chromatographed on a DEAE-sepharose column (acetate form), eluting with a linear gradient from 0 to 1 M $NH_4OAc$, pH 5.6. Fractions were assayed for absorbance at 260 nm, showing three main products eluting from the column. Fractions containing the middle product were pooled and lyophilized. The solid was redissolved in $H_2O$ and purified to homogeneity by $C_{18}$ reverse phase HPLC (3 mL/min; 0 to 10 min, 20 mM NaOAc, pH 5.6; 10 to 18 min, a linear gradient to 15% MeOH; 18 min onward, 15% MeOH; elution time: 23.3 min). Fractions containing product were concentrated to 20 mL and added to 80 mL of −20° C. acetone, yielding 122 mg (29% from NADP) of precipitate: $^1H$ NMR ($D_2O$, 400 MHz) δ9.19 (s, 1H), 8.98 (d, J=6.3, 1H), 8.86 (s, 1H), 8.74 (d, J=8.1, 1H), 8.57 (d, J=6.3, 1H), 8.25 (s, 1H), 8.15 (d, J=9.7, 1H), 8.07 (t, J=4.7, 1H), 7.85 (s, 1H), 7.40 (dd, J=, 1H), 6.01 (d, J=6.7, 1H), 5.90 (d, J=4.5, 1H), 5.38 (d, J=5.4, 1H), 4.70 (m, 2H), 4.39 (t, J=5.1, 1H), 4.22–4.04 (m, 5H), 1.73 (s, 3H); $\epsilon_{355}$=200 $M^{-1}$ $cm^{-1}$; HRMS (FAB, $M.NH_4^+$) calc for $C_{29}H_{38}N_9O_{21}P_3$ 941.1395, found 941.1404.

Example 4

Synthesis of N-(α-Carboxy-2-nitrobenzyl)-nicotinamide adenine dinucleotide (CNB-NAD, 4)

NAD (266 mg, 0.40 mmol) and NHS nicotinate (600 mg, 2.73 mmol) were treated essentially as in the two-step process described in Example 3. Product was eluted from the DEAE column with a linear gradient from 0 to 600 mM $NH_4OAc$, pH 5.6. Precipitation following purification to homogeneity by $C_{18}$ reverse phase HPLC (3 mL/min; 0 to 10 min, 20 mM NaOAc; 10 to 17 min, up to 20% MeOH; 17 min onward, 20% MeOH; elution time: 24.4 min) yielded 71 mg (21% from NAD) of white solid: $^1H$ NMR ($D_2O$, 400 MHz) δ9.25 (s, 1H), 9.05 (d, J=6.3, 1H), 8.81 (s, 1H), 8.78 (d, J=8.2, 1H), 8.54 (d, J=3.7, 1H), 8.25 (s, 1H), 8.11 (m, 2H), 7.85 (s, 1H), 7.37 (dd, J=8.0,5.1, 1H), 6.07 (d, J=6.6, 1H), 5.85 (d, J=4.2, 1H), 5.40 (d, J=4.2, 1H), 4.49 (d, J=5.2, 1H), 4.32 (d, J=4.2, 1H), 4.26–4.02 (m, 6H), 1.73 (s, 3H); HRMS (FAB, $MNa^+$) calc for $C_{29}H_{33}N_8O_{18}P_2Na$ 866.1286, found 866.1271.

Example 5

Photolysis

Samples were excited with a Q-switched frequency-tripled Quanta-Ray DCR-11 Nd:YAG laser (55 mJ per 8-ns pulse). The actinic light pulse was focused onto the sample cell, a quartz cuvette with a 2-mm excitation path length and a 10-mm detection path length, with a cylindrical lens, forming an ellipse with radii of 2 mm and 7 mm. Samples were prepared to have an absorbance of 0.20 at 355 nm. Transient differential absorption spectra were recorded as the sum of 100 individual laser shots following excitation at 355 nm, with a 100-ns recording delay between excitation and detection. Intermediates were detected using a Hamamtsu xenon arc lamp orthogonal to the actinic beam, which produced two equal-intensity probe beams directed onto the sample by a bifurcated quartz fiber bundle. Each light was detected separately by a Princeton Instruments DIDA-512 Intensified Dual Diode Array Detector, which has a gate duration of 5 ns. Recording delays between laser pulse and probe light were varied with an EG&G 9658 Digital Delay Generator. The raw data were ratioed and converted to absorbance.

Figure 6:
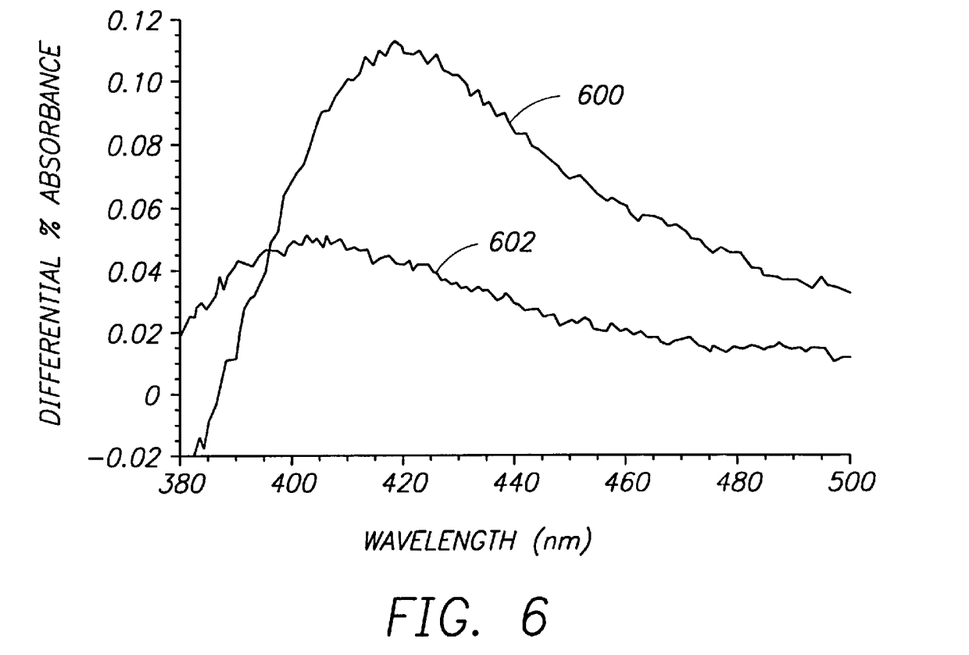
FIG. 6 shows the differential absorption spectra of nicotinamide-caged CNB-NADP and phosphate-caged DMNPE-NADP following excitation by 355-nm laser pulse according to a preferred embodiment of the present invention.

Confirmation that caged compounds according to the present invention produce NAD/P following photolysis was obtained by several methods. FIG. 6 shows the differential absorption spectra of nicotinamide-caged CNB-NADP 3 and phosphate-caged DMNPE-NADP 1 following excitation by 355-nm laser pulse. The broad absorption peaks in the 400–420 nm range are characteristic of the aci-nitro anions (402, FIG. 4) produced following photolysis of 2-nitrobenzyl compounds. Transients from the DMNPE compound (trace 600) shows peak absorbances at 418 nm, while the CNB transient 602 is centered at 402 nm.

Figure 7:
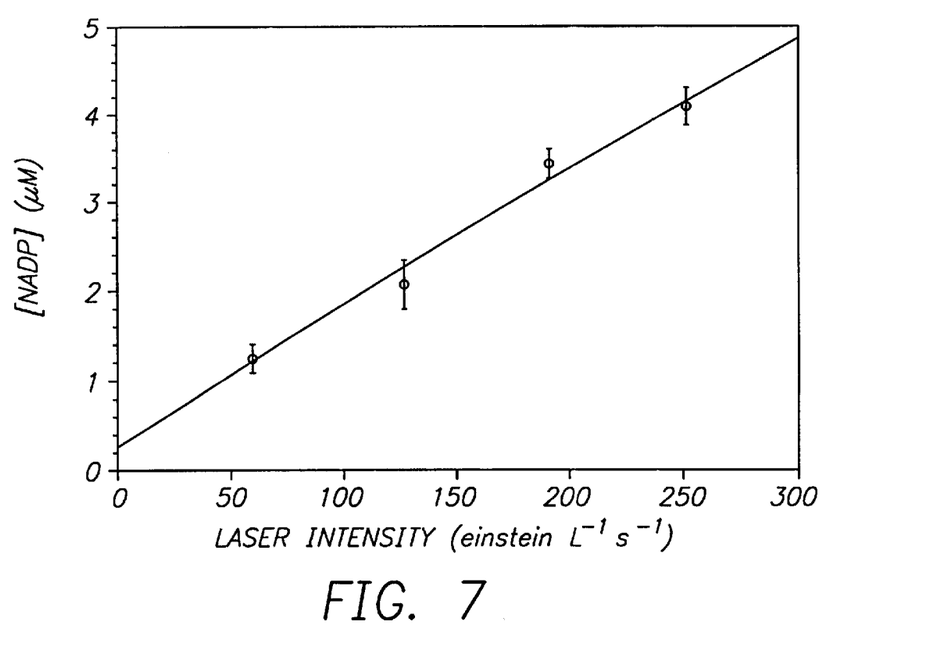
FIG. 7 shows NADP concentration as a function of laser intensity for the photolysis of caged-NADP according to a preferred embodiment of the present invention.

FIG. 7 shows NADP concentration as a function of photolytic laser intensity. A final concentration of 4.1 μM NADP is produced at the full laser energy of 55 mJ following a total of 800 ns of excitation of compound 1. This represents photorelease of 72% of the caged NADP in an elliptical cylinder irradiated by an actinic beam. The percentage of product release was calculated from the G6PD assay (Bernofsky, C. and Swan, M. (1973) *Anal. Biochem.* 53, 452–458; Nisselbaum, J. S. and Green, S. (1969) *Anal. Biochem.* 27, 212–217) which indicated a final concentration of 4.1 μM NADP was produced from an initial concentration of 51 μM of 1(calculated with known values for $A_{355}$ and $\epsilon_{355}$ of 0.20 and 3900 $M^{-1}$ $cm^{-1}$), representing photorelease of 7.9% of compound 1 in the cuvette. The volume of the elliptical cylinder irradiated by the actinic beam was 88 μL of the 800-μL sample, meaning that 72% of the irradiated caged compound was converted to NADP. Similar values for Φ and $\epsilon_{355}$ were observed for DMNPE-caged NAD (2), indicating that significant amounts of NADP and NAD can be released from the DMNPE-caged compounds on very short timescales.

Figure 8:
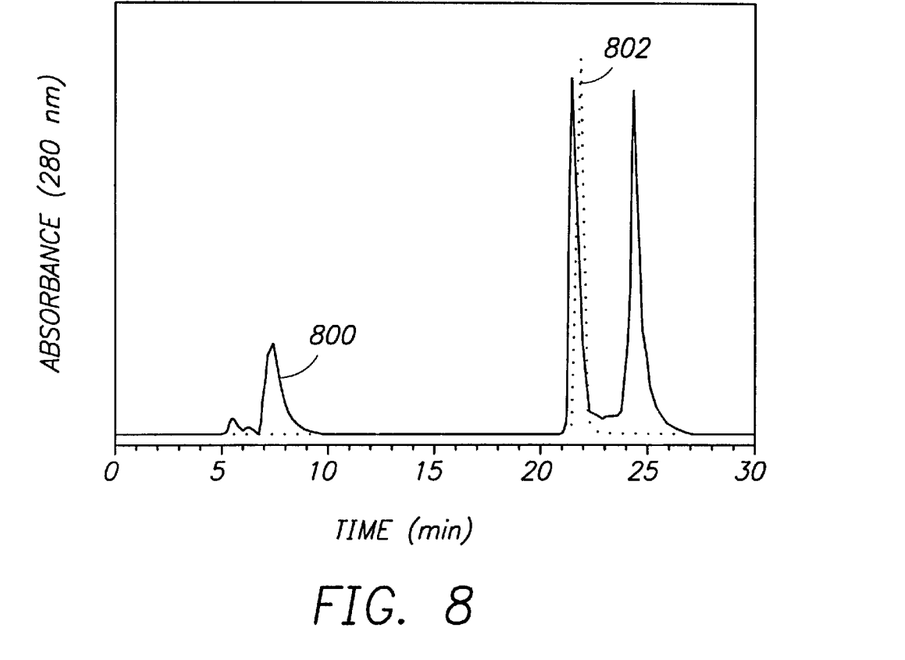
FIG. 8 shows a reverse phase HPLC chromatogram produced by analysis of solutions of irradiated caged CNB-NAD according to a preferred embodiment of the present invention.

For the CNB-caged compounds (3 and 4), formation of NADP and NAD was confirmed by reverse phase HPLC analysis of solutions of irradiated caged compounds. The HPLC trace of a partially photolyzed sample of CNB-NADP 3 contains a new peak with a retention time of 11.1 min, which corresponds to the retention time of commercially available NADP. As shown in FIG. 8, the CNB-NAD 4 trace 800 similarly includes a new peak at 21.9 min corresponding to NAD (the dotted trace 802 is the peak for commercial NAD). Both traces include new peaks at 7.5 min, the reported retention time of the ketoacid photoproduct (404, FIG. 4) under similar elution conditions.

Finally, NADP is present in X-ray structures (described below) of IDH with either photolyzed 1 or 3.

Example 6

Kinetics

The rates of photorelease for compounds 1, 2, and 3 were determined by measurement of the rates of decay of the aci-nitro anions produced following photolysis. The decay of aci-nitro intermediates was monitored at 402 nm or 418 nm with an Osram 50-W tungsten halogen lamp following excitation at 355 nm with a 55 mJ 8-ns pulse. Samples were prepared with 50 mM phosphate buffer, pH 7.0 or pH 6.0. A total of 256 individual laser shots were averaged for each sample, and the corresponding baseline, recorded without laser excitation, was subtracted for each measurement. Kinetic analysis was made by nonlinear, least-squares computer iteration. The averages of three trials are reported.

Figure 9:
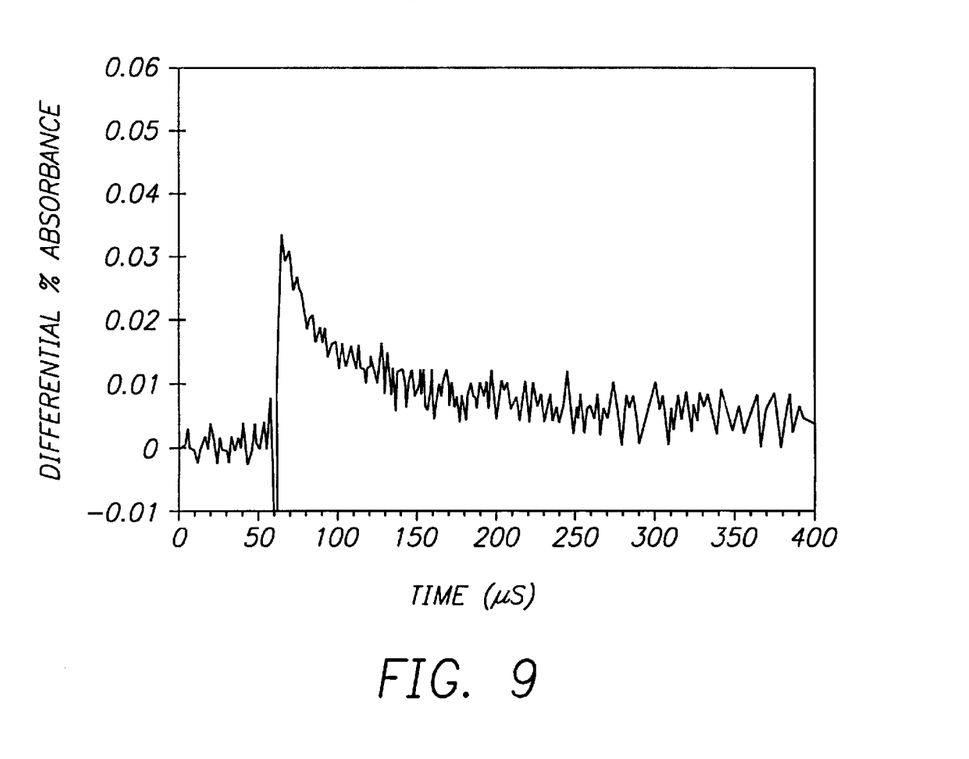
FIG. 9 shows a spectrophotometric output illustrating the spectral changes at 418 nm following photolysis of DNMPE-NADP according to a preferred embodiment of the present invention.

The spectral changes at 418 nm following photolysis of 1 are shown in FIG. 9. Photolyzed DMNPE-caged samples all showed a rapid rise in absorbance characteristic of aci-nitro anion formation, followed by decays which were best fit to double exponential functions. Photolysis of 1 in the presence of 10 mM DTT produced a transient with decay rates of $1.3 \times 10^4$ s$^{-1}$ and 93 s$^{-1}$. Raising DTT concentration to 100 mM increased the slow component five-fold to 480 s$^{-1}$ while only marginally increasing the fast component to $1.8 \times 10^4$ s$^{-1}$. DMNPE-NAD (2) showed a fast decay component of $1.7 \times 10^4$ s$^{31\ 1}$.

The transient produced by photolysis of 3 exhibited first-order decay kinetics at rates considerably slower than those for 1 (k=30 s$^{-1}$). Decrease of the sample pH to 6 marginally increased the rate of photorelease to 42 s$^{-1}$, which is consistent with literature reports of a mild pH dependence of k for CNB-caged compounds.

Example 7

Crystallographic analysis of 1 and 3 with IDH

IDH was purified and crystallized as described previously by Reeves, H. C., Daumy, G. O., Lin, C. C., and Houston, M. (1972) *Biochim. Biophys. Acta* 258, 27–39; LaPorte, D. C., Thorsness, P. E., and Koshland, D. E., Jr. (1985) *J. Biol. Chem.* 260, 10563–10568; Hurley, J. H., Thorsness, P. E., Ramalingam, V., Helmers, N. H., Koshland, D. E., Jr., and Stroud, R. M. (1989) *Proc. Natl. Acad. Sci. U.S.A* 86, 8635–8639; and Stoddard, B. L., Dean, A., and Koshland, D. E., Jr. (1993) *Biochemistry* 32, 9310–9316.

The crystals were 0.5 to 1.5 mm along their longest edges, with a shorter third dimension of 0.2 to 0.3 mm; the crystals belong to space group P4$_3$2$_1$2. The unit cell dimensions prior to photolysis and after binding liberated substrate consistently refined to values within 0.5% of the previously published lengths during data processing.

A total of six crystallographic data sets were collected for this study. The structure of the enzyme was determined prior to photolysis after soaking with each compound, both in the presence and absence of bound isocitrate/Mg$^{+2}$. The structure of the bound photolysis product was also determined for both caged compounds in the absence of isocitrate/Mg$^{+2}$.

For each experiment, a crystal was transferred to 0.5 mL of a stabilization solution (generally 10% higher ammonium sulfate than that used to grow the crystals, buffered at pH 7.0 with HEPES) and soaked overnight in the dark with 250 mM of either 1 or 3. These experiments were performed for each compound in the presence and absence of 50 mM isocitrate and MgSO$_4$. To protect the crystal from oxidative degradation after photolysis by the nitroso photoproducts, β-mercaptoethanol (10 mM) and DTT (10 mM) were also added to the mother liquor. The crystals were mounted under safe-light in quartz capillaries with mother liquor at either end of the capillary. The mount was sealed with mineral oil and paraffin wax. Initial data were collected at room temperature in the dark on an RAXIS imaging plate area detector with a Rigaku RU-200 rotating anode X-ray generator operating at 50 kV, 80 mA. A complete data set was collected from each crystal to 2.5 Å resolution using 20 1.5° rotations at 30 minutes per frame, followed by an additional 10 frames collected with the crystal on a 45° jig (Molecular Structure Corporation) for completeness. The total decay in X-ray intensities during collection of each of these four dark data sets was less than 5% of the initial structure average factor amplitudes.

Crystals that were soaked in caged 1 or 3 in the absence of isocitrate were each irradiated after the dark data collection, using a two minute exposure with a Cole Parmer 9741-50 quartz halogen light source with a 9741-03 high intensity 150 watt bulb and dual fiber optic light pipes and focusing lenses. The crystal was irradiated from two directions simultaneously, 90 degrees apart in order to maximize efficient excitation of each compound in the crystal lattice. A second data set was then collected after photolysis with an identical strategy to that described above.

For all six final data sets, between 88% and 95% of the unique data were present in the final data set. The RAXIS data collection software package (Molecular Structure Corporation) was used to collect and process the data, and all refinements and protein difference Fourier map calculations were conducted with XPLOR, as described in Brunger, A. T., Kuriyan, J., and Karplus, M. (1987) *Science* 235, 458–460.

The initial coordinates of IDH for refinement and subsequent difference map calculation were the structure of wild-type apoenzyme taken from the Brookhaven PDB (Bernstein, F. C., Koetzle, T. F., Williams, G. J., Meyer, E. E., Jr., Brice, M. D., Rodgers, J. R., Kennard, O., Shimanouchi, T., and Tasumi, M. (1977) *J. Mol. Biol.* 112, 535–542), with accession number 3ICD. The data were placed into an XPLOR simulated annealing refinement using the structure of uncomplexed IDH as the initial model. Refinement was performed against the data set from 50 to 2.5 Å resolution. A protocol in which the structure, after the initial static energy minimization, is heated to 4000° C. and then immediately placed into a slow cooling (50 ps) annealing minimization was used. No extended dynamics were performed during the heat stage of the refinement.

After this initial round of refinement, difference Fourier syntheses with the coefficients $[F_{o\ (soaked\ crystals,\ dark)} - F_{c\ (apo\ enzyme)}]\alpha_{calc}$ were calculated using the experimentally measured structure factor amplitudes for the soaked enzyme prior to irradiation. Phases and structure factors for the difference Fourier map were calculated using only the protein model. For those difference maps which showed the presence of bound cofactor before or after photolysis, the visible portions of the molecule were built and the refinement was continued. After a second round of refinement and rebuilding, final residual $F_o - F_c$ difference maps were calculated and examined for any unmodeled density. A small number of water molecules (less than 30 for each structure) were placed, and the refinement was continued. Restrained individual B-factors were refined for each structure.

FIGS. 10A–F show electron density maps of crystallographic studies of CNB-NADP (3) and DMNPE-NADP (1) binding to the active site of IDH. All figures are of $F_o - F_c$ difference Fourier omit maps calculated at the end of refinement. All panels were contoured at 2σ density, except for FIGS. D and E, which were contoured at 1 σ to more closely examine the map for bound cofactor. Features of electron density were excluded from the regions of the enzyme side chains for clarity, but were otherwise unmodified.

Figure 10:
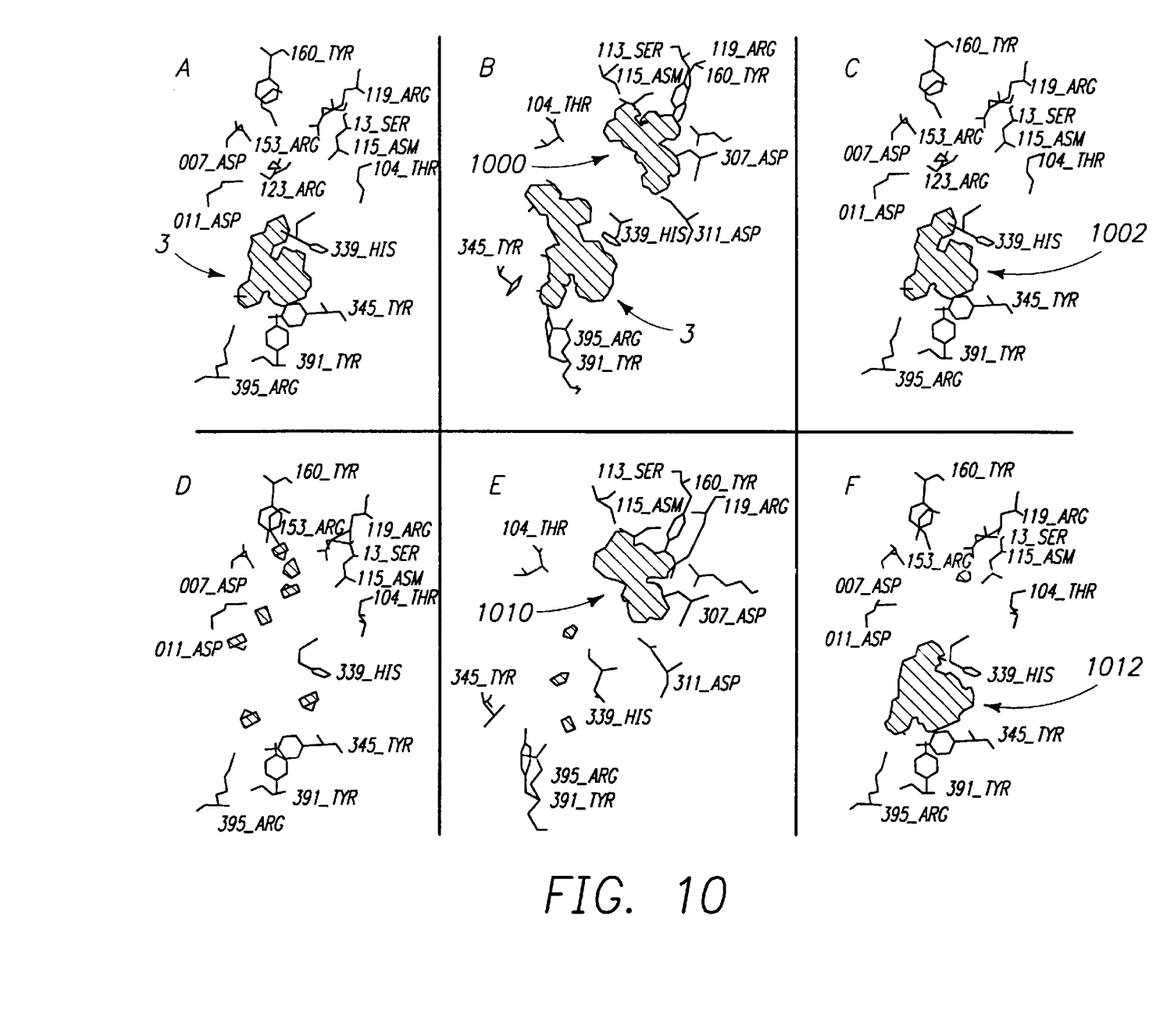
FIG. 10A shows an electron density map for nicotinamide-caged compound 3 binding to the enzyme through interactions between the adenosyl ring and adjoining phosphoryl-ribose.
FIG. 10B shows a map of compound 3 when soaked into crystals in the presence of bound isocitrate/$Mg^{+2}$.
FIG. 10C shows a map for compound 3 after photolysis in the absence of isocitrate.
FIG. 10D shows an electron density map for phosphate-caged compound 1 which fails to bind to IDH when soaked into crystals in the absence of bound isocitrate/$Mg^{+2}$.
FIG. 10E shows a map for compound 1 which also fails to bind to IDH when soaked into crystals in the presence of bound isocitrate/$Mg^{+2}$.
FIG. 10F shows a map for compound 1 after photolysis.

FIGS. 10A shows that nicotinamide-caged compound 3 binds to the enzyme through interactions between the adenosyl ring and adjoining phosphoryl-ribose, as previously shown for unmodified NADP. The nicotinamide ring, its ribose sugar, and the first backbone phosphate are all completely disordered. When the same caged compound (3) is soaked into crystals in the presence of bound isocitrate/Mg$^{+2}$, 1000 both backbone phosphates of the caged cofactor are well ordered in a difference map, as shown in FIG. B, indicating that the nicotinamide group and its ribose are more strongly attracted to its binding site in the presence of the substrate. The presence of the caging group on the carboxyamide nitrogen sterically prevents hydride transfer. That the turnover does not occur under these conditions (through the presence of contaminating bound NADP) was verified by absorbance analysis of dissolved crystals after extensive soaks, as well as by the fact that the crystals do not crack or dissolve (data not shown). After photolysis in the absence of isocitrate, liberated NADP 1002 is still bound to the active site as previously determined for unmodified NADP, as shown in FIG. C. The clear advantage of this compound as a photolytic trigger for time-resolved studies is that it is bound to the enzyme active site prior to photolysis, so that no additional diffusion or binding events are necessary to form the Michaelis complex.

Phosphate-caged compound 1 fails to bind to IDH when soaked into crystals in the absence (FIG. D) or presence (FIG. E) of bound isocitrate/Mg$^{30\ 2}$ 1010. Photolysis of the compound in the crystal, however, generates a normal enzyme-NADP complex 1012 (FIG. F). While this compound must bind to the enzyme active site after release as part of the mechanism of catalytic triggering, it is both fast and extremely efficient for photodissociation.

Conclusion

The rates of NADP and NAD formation from DMNPE-caged compounds 1 and 2 are similar to the rate of photolysis of DMNPE-caged phosphate (Wootton, J. F. and Trentham, D. R. (1989) in *NATO Advanced Research Workshop on Photochemical Probes in Biochemistry* (Nielsen, P. E., Ed.) pp 277–296, Kluwer Academic Publishers, Boston), but considerably faster than the rates of DMNPE-caged ATP and glycine photolysis (Wilcox, M., Viola, R. W., Johnson, K. W., Billington, A. P., Carpenter, B. K., McCray, J. A., Guzikowski, A. P., and Hess, G. P. (1990) *J. Org. Chem.* 55, 1585–1589). They are also significantly faster than the turnover rate of IDH within the crystal at pH 7 (38 s$^{-1}$, (Bolduc, J. M., Dyer, D. H., Scott, W. G., Singer, P., Sweet, R. M., Koshland, D. E., Jr., and Stoddard, B. L. (1995) *Science* 268, 1312–1318)), indicating that the rate of photolysis for 1 will not be a limiting factor in triggering synchronized IDH turnover. Use of the DMNPE caging group seems to have been largely abandoned following the initial reports of disappointing photochemical characteristics for DMNPE-ATP and DMNPE-glycine. However, the inventors of the present application have shown that DMNPE-aged compounds are capable of rapid release rates and extensive product formation. Such compounds may find use in a variety of biomedical research procedures.

Previous unsuccessful attempts to cage NAD/P by a direct route using NADase have been solved by synthesizing nicotinamide-caged CNB-NADP 3 and CNB-NAD 4 by a two-step process starting with the NADase-catalyzed exchange of activated ester NHS nicotinate onto NADP or NAD, yielding NHS-NAD/P. In the second step of the present synthesis, crude NHS-NAD/P may be treated with 2-nitrophenylglycine following the first step, to produce caged CNB-NAD/P.

For general use, the phosphate-caged DMNPE compounds offer definite advantages over the nicotinamide-caged CNB compounds. In addition to having a much faster photolysis rate, DMNPE-NADP's quantum yield and is about twice that of CNB-NADP, and its value of $\epsilon_{355}$ is twenty-fold greater. Taken together, these two pieces of data indicate that an approximately 400-fold lower concentration of 1 than 3 would be required to produce the same concentration of NADP following excitation at 355 nm. Nevertheless, the nicotinamide-caged CNB compounds have also been demonstrated to effectively cage NAD/P, and CNB-NADP has been shown to exhibit "catalytic caging" with at least one enzyme (IDH). This has the advantage when the compound is used as a photolytic trigger for time-resolved studies that it is bound to the enzyme active site prior to photolysis, so that no additional diffusion or binding events are necessary to form the Michaelis complex.

Further characterization of the compounds of the present invention is contained in Cohen, B. E., Stoddard, B. L. and Koshland, D. E., Jr. (1997) *Biochemistry* 36, 9035–9044, which is incorporated by reference herein for all purposes.

Although the foregoing invention has been described in some detail for purposes of clarity of understanding, it will be apparent that certain changes and modifications may be practiced within the scope of the appended claims. For example, photolabile caging groups other than DNMPE or CNB may also be used. It should be noted that there are may alternative ways of implementing both the process and apparatus of the present invention. Accordingly, the present embodiments are to be considered as illustrative and not restrictive, and the invention is not to be limited to the details given herein, but may be modified within the scope and equivalents of the appended claims.

What is claimed is:

1. A photolabile compound, comprising:

a pyridine nucleotide coenzyme covalently bonded to a 2-nitrobenzyl family caging group.

2. A compound according to claim 1, wherein said pyridine nucleotide coenzyme is nicotinamide adenine dinucleotide phosphate.

3. A compound according to claim 2, wherein said 2-nitrobenzyl family caging group is 1-(4,5-dimethoxy-2-nitrophenyl)ethyl.

4. A compound according to claim 3, wherein said 1-(4,5-dimethoxy-2-nitrophenyl)ethyl is bound to a 2'-phosphate group of said nicotinamide adenine dinucleotide phosphate.

5. A compound according to claim 2, wherein said 2-nitrobenzyl family caging group is α-carboxy-2-nitrobenzyl.

6. A compound according to claim 5, wherein said α-carboxy-2-nitrobenzyl is bound to the nicotinamide group of said nicotinamide adenine dinucleotide phosphate.

7. A compound according to claim 1, wherein said pyridine nucleotide coenzyme is nicotinamide adenine dinucleotide.

8. A compound according to claim 7, wherein said 2-nitrobenzyl family caging group is 1-(4,5-dimethoxy-2-nitrophenyl)ethyl.

9. A compound according to claim 8, wherein said 1-(4,5-dimethoxy-2-nitrophenyl)ethyl is bound to a backbone phosphate group of said nicotinamide adenine dinucleotide.

10. A compound according to claim 7, wherein said 2-nitrobenzyl family caging group is α-carboxy-2-nitrobenzyl.

11. A compound according to claim 10, wherein said α-carboxy-2-nitrobenzyl is bound to die nicotinamide group of said nicotinamide adenine dinucleotide phosphate.

12. A compound according to claim 1, having the following structure:

13. A compound according to claim 1, having the following structure:

14. A compound according to claim 1, having the following structure:

wherein $R^1$ is one of (–) and and, $R^2$ is the other of (–)

wherein R is one of $PO_3^{-2}$ {SALT$^{2+}$} and H.

15. A method of making a photolabile compound chemical compound which fragments into a biologically active compound upon, comprising:
providing a pyridine nucleotide coenzyme; and
binding a 2-nitrobenzyl family caging group to said nucleotide.

16. A method according to claim 15, wherein said pyridine nucleotide coenzyme is nicotinamide adenine dinucleotide phosphate and said 2-nitrobenzyl family caging group is 1-(4,5-dimethoxy-2-nitrophenyl)ethyl.

17. A method according to claim 16, comprising:
combining 1-(4,5-dimethoxy-2-nitrophenyl)diazoethane dissolved in organic media with an aqueous solution of nicotinamide adenine dinucleotide phosphate at a pH of about 4; and
agitating the combination.

18. A method according to claim 15, wherein said pyridine nucleotide coenzyme is nicotinamide adenine dinucleotide and said 2-nitrobenzyl family caging group is 1-(4,5-dimethoxy-2-nitrophenyl)ethyl.

19. A method according to claim 18, comprising:
combining 1-(4,5-dimethoxy-2-nitrophenyl)diazoethane dissolved in organic media with an aqueous solution of an alkylated nicotinamide adenine dinucleotide.

20. A method according to claim 15, wherein said pyridine nucleotide coenzyme is nicotinamide adenine dinucleotide phosphate and said 2-nitrobenzyl family caging group is α-carboxy-2-nitrobenzyl.

21. A method according to claim 20, comprising:
combining nicotinamide adenine dinucleotide phosphate with NADase and NHS nicotinate, whereby NADase catalyzes an exchange of N-hydroxysuccinimide nicotinate onto nicotinamide adenine dinucleotide phosphate, yielding N-hydroxysuccinimide-nicotinamide adenine dinucleotide phosphate; and
treating, said N-hydroxysuccinimide-nicotinamide adenine dinucleotide phosphate with 2-nitrophenylglycine.

22. A method according to claim 15, wherein said pyridine nucleotide coenzyme is nicotinamide adenine dinucleotide and said 2-nitrobenzyl family caging group is α-carboxy-2-nitrobenzyl.

23. A method according to claim 20, comprising:
combining nicotinamide adenine dinucleotide with NADase and NHS nicotinate, whereby NADase catalyzes an exchange of N-hydroxysuccinimide nicotinate onto nicotinamide adenine dinucleotide, yielding N-hydroxysuccinimide-nicotinamide adenine dinucleotide; and treating, said N-hydroxysuccinimide-nicotinamide adenine dinucleotide with 2-nitrophenylglycine.

* * * * *